US00PP26043P3

(12) United States Plant Patent
Van Rosmalen

(10) Patent No.: US PP26,043 P3
(45) Date of Patent: Nov. 3, 2015

(54) *PHALAENOPSIS* ORCHID PLANT NAMED 'PHALDETAM'

(50) Latin Name: ***Phalaenopsis* hybrid**
Varietal Denomination: PHALDETAM

(71) Applicant: ANTHURA B.V., Bleiswijk (NL)

(72) Inventor: Nicolaas Arnoldus Maria Van Rosmalen, Velp (NL)

(73) Assignee: ANTHURA B.V., Bleiswijk (NL)

( * ) Notice: Subject to any disclaimer, the term of this patent is extended or adjusted under 35 U.S.C. 154(b) by 249 days.

(21) Appl. No.: 13/986,991

(22) Filed: Jun. 21, 2013

(65) Prior Publication Data

US 2014/0380540 P1 Dec. 25, 2014

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

U.S. PATENT DOCUMENTS

PP24,364 P3 * 4/2014 Schoone ..... Plt./311

OTHER PUBLICATIONS

Enclosure for the Plant Patent application of Anthura BV, 13 pages 2015.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALDETAM', particularly characterized by white flowers with purple flecks and white lip with yellow and purple shade, 1 to 2 peduncles, a long and sturdy inflorescence, a narrow obovate leaf shape, and propagated by tissue culture is disclosed.

3 Drawing Sheets

Genus and species: *Phalaenopsis* hybrid.
Variety denomination: 'PHALDETAM'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDETAM'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDETAM' is particularly characterized by its attractive and unique white flowers with purple spots, economical propagation by tissue culture, rapid growth, and a plant dimension suitable for packaging and shipping to the market.

'PHALDETAM' is a product of a planned breeding program conducted in Bleiswijk, The Netherlands.

The new *Phalaenopsis* 'PHALDETAM' originated from a cross made in August 2008 in Bleiswijk, The Netherlands. The female parent is a white with purple flecks *Phalaenopsis* pot plant name '01-1758' (unpatented), while the male parent is a white *Phalaenopsis* pot plant named '06285-01' (unpatented). A single plant was selected in October 2008 and has been asexually reproduced repeatedly by meristem tissue culture in Bleiswijk, The Netherlands over a 5-year period. The new variety has been found to retain its distinctive characteristics through successive asexual propagations.

Asexual reproduction of 'PHALDETAM' by meristem tissue culture was first performed in October 2011 in Bleiswijk, The Netherlands and has demonstrated that the new cultivar is firmly fixed and retained through successive generations of asexual reproduction.

Plant Breeder's Rights for this variety have been applied for in Europe on Jan. 15, 2013. 'PHALDETAM' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) White flower with purple flecks and white lip with yellow and purple shade;
2) 1 to 2 peduncles;
3) Inflorescence is long and sturdy;
4) The shape of the leaf is narrow obovate; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in March 2013.

DESCRIPTION OF THE NEW VARIETY

Figure 1:
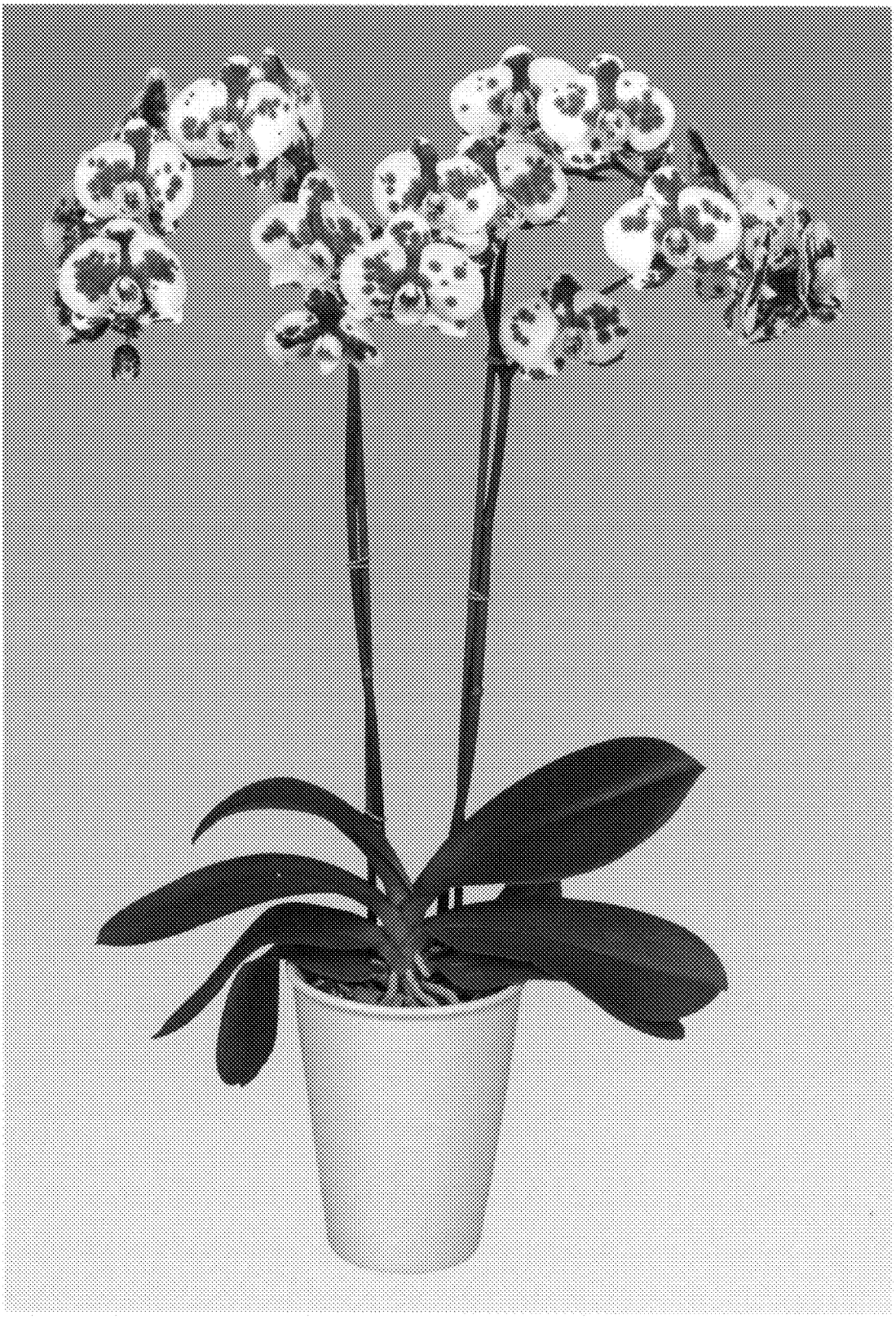
FIG. 1 shows the overall plant habit, including blooms, buds and foliage of 'PHALDETAM'.
Figure 2:
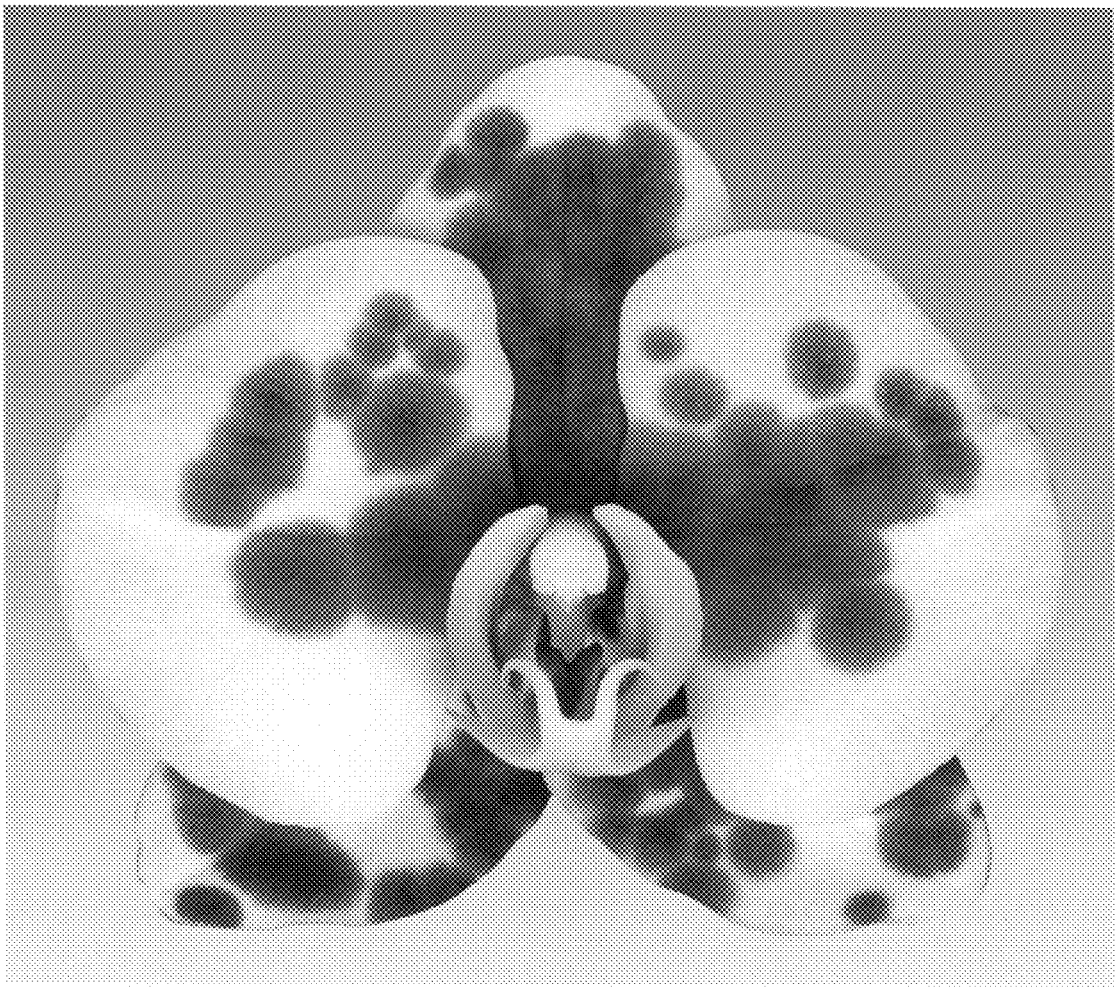
FIG. 2 shows a close-up of the flower of 'PHALDETAM'.
Figure 3:
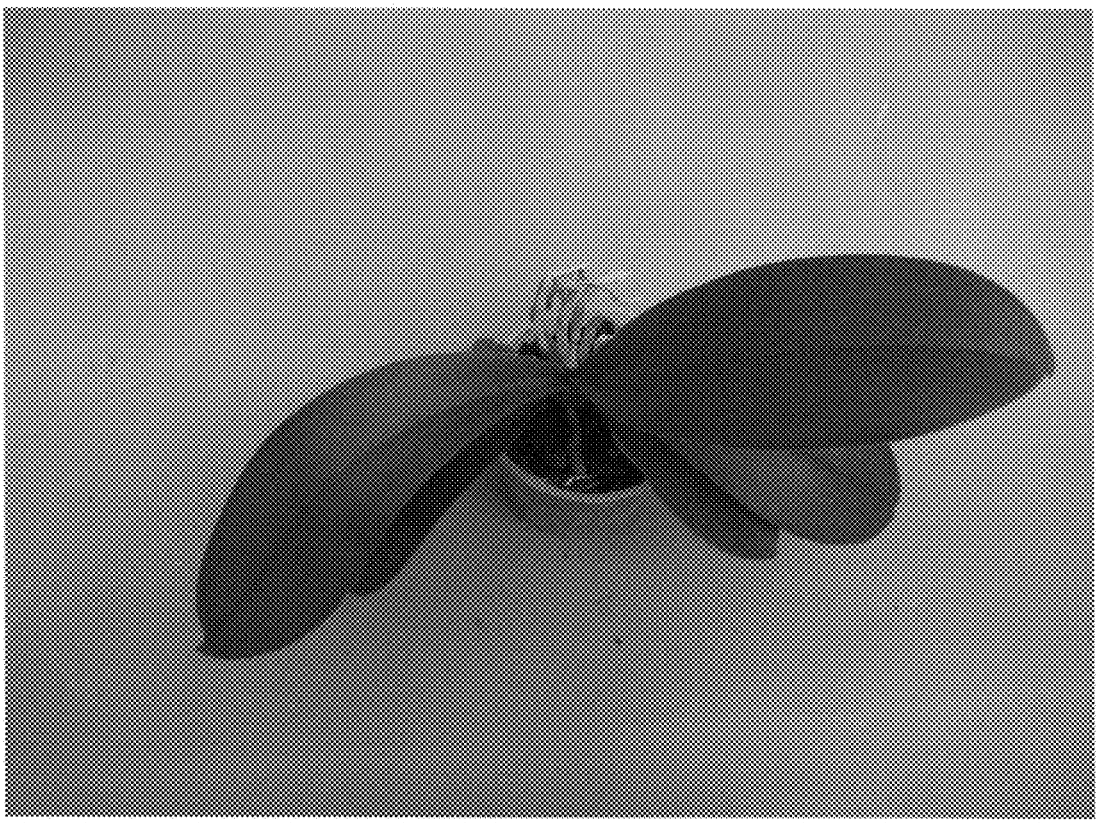
FIG. 3 shows a close-up of the leaves of 'PHALDETAM'.

The following detailed description sets forth the distinctive characteristics of 'PHALDETAM'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in March 2013. Color readings were taken under 4000 till 6000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family.*—Orchidaceae.

*Botanical.*—*Phalaenopsis* hybrid.

*Common name.*—*Phalaenopsis.*

*Variety name.*—'PHALDETAM'.

Parentage:

*Female parent.*—*Phalaenopsis* cultivar '01-1758' (unpatented).

*Male parent.*—*Phalaenopsis* cultivar '06285-01' (unpatented).

Propagation:

*Type.*—Meristem tissue culture.

Plant:

*Crop time* (*time to produce a finished flowering plant*).—48 to 50 weeks for a 12 cm pot.

*Growth habit of inflorescence.*—Standard type, green leaves and normal raceme.

*Height* (*including pot, including inflorescence*).—65.0 cm to 70.0 cm.

*Width* (*measured from leaf tips*).—40.0 cm to 45.0 cm.

*Vigor.*—Moderate.

Roots:

*Root description.*—Grey-green-colored roots with light branching lateral roots having grey-green-colored root tips.

Leaves:

*Mature leaves.*—Quantity per plant: 5 to 6 leaves are produced before flowering. Length (fully expanded): 21.0 cm to 24.0 cm. Width: 7.0 cm to 8.5 cm. Shape: Narrow obovate. Apex: Mucronate. Leaf blade angle with the petiole: Between 40 degrees and 70 degrees. Leaf margin: Entire. Color: Upper surface: RHS 137B. Lower surface: RHS 138B. Texture: Smooth. Thickness: 2.5 mm. Venation: Pattern: Parallel. Color of the midvein: Upper surface: RHS 137A. Lower surface: RHS 138C.

Peduncle:

*Quantity per plant.*—1 to 2.

*Number of flowers per peduncle.*—14 to 24.

*Length.*—55.0 cm to 65.0 cm.

*Diameter.*—About 0.6 cm.

*Strength.*—Strong.

*Aspect.*—Upright.

*Texture.*—Smooth.

*Color.*—Green (RHS 146A) and slightly brown (RHS 200A).

*Internode length.*—60.0 mm to 110.0 mm.

Inflorescence description:

*Appearance.*—Upright to slightly pendant, raceme inflorescence with bilaterally symmetrical flowers that open in succession beginning with the lowermost flower.

*Inflorescence size.*—Height (from base to tip): 110.0 mm to 140.0 mm. Diameter: 200.0 mm to 220.0 mm.

*Flowering time.*—First flowers can be expected 10 to 11 months after planting in a 12 cm pot, as mentioned in the botanical description.

*Flower bud.*—Average size: Medium. Length: 1.9 cm to 2.0 cm. Width: 17.0 mm to 18.0 mm. Shape: Egg shape. Color designation: Yellow-green (RHS 150C) with greyed-purple flecks (RHS 187A).

*Flower.*—Height: 80.0 mm to 90.0 mm. Diameter: 80.0 mm to 90.0 mm. Depth of lip: 25.0 mm to 27.0 mm.

*Flower longevity.*—On the plant: 10 to 14 weeks.

*Fragrance.*—Absent.

*Petals.*—Arrangement: Open. Shape: Semi-circular. Apex: Mucronate to rounded, slightly asymmetric. Margin: Slightly undulate. Length: 52.0 mm to 56.0 mm. Width: 36.0 mm to 40.0 mm. Color (when fully opened): Upper surface: White (RHS 155C) with purple flecks (RHS 79A and 71A). Lower surface: White (RHS 155C) with purple flecks (RHS 81A) diluted around the edge of the flecks.

*Dorsal sepal.*—Shape: Elliptic. Apex: Rounded to emarginated. Length: 40.0 mm to 42.0 mm. Width: 33.0 mm to 35.0 mm. Color (when fully opened): Upper surface: White (RHS 155C) with purple flecks (RHS 79A and 71A). Lower surface: White (RHS 155C) with purple flecks (RHS 77A) diluted around the edge of the flecks.

*Lateral sepals.*—Shape: Ovate. Apex: Obtuse. Length: 32.0 mm to 34.0 mm. Width: 47.0 mm to 49.0 mm. Color (when fully opened): Upper surface: Basic color: White (RHS 155C) with purple flecks (RHS 79A and 71A). Over color: Slightly yellow-green (RHS 150C/150D) towards the center of the flower. Lower surface: Basic color: White (RHS 155C) with purple flecks (RHS 77A) diluted around the edge of the flecks. Over color: Yellow-green (RHS 145D) on one side towards the center.

*Labellum* (*lip*).—Margin: Entire and slightly undulate. Length: 26.0 mm to 28.0 mm. Width (measured at apical lobe): 18.0 mm to 20.0 mm. Pubescence: Absent. Whiskers: Length: 1.3 cm to 1.5 cm. Color: White (RHS 155C) with yellow tips (RHS 4D).

*Lateral lobe.*—Length: 2.0 cm to 2.2 cm. Width: 1.1 cm to 1.3 cm. Shape: type V (as described in the International Union for the Protection of New Varieties of Plants (UPOV) Test Guidelines for *Phalaenopsis*); spatulate. Color: White with yellow and purple shade (RHS 155C, 2B, 59A).

*Apical lobe.*—Length: 2.0 cm to 2.2 cm. Width: 1.9 cm to 2.1 cm. Shape: Obdeltoid. Color: White with yellow shade (RHS 155C, 2B).

*Callus.*—Average size: Medium. Height: 0.7 cm. Length: 0.5 cm. Width: 0.4 cm. Color: Dark purple (RHS 79A).

Reproductive organs:

*Arrangement.*—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column.*—Length: 11.0 mm to 12.0 mm. Diameter: 5.5 mm to 6.5 mm. Color: White (RHS 155C).

*Pollinia.*—Quantity: 2. Size: 1.4 mm to 1.5 mm. Color: Orange (RHS 23A).

*Ovary.*—Length: 8.0 mm to 9.0 mm (cutted open). Diameter: 4.5 mm to 5.5 mm.

*Pedicel.*—Length: 32.0 mm to 38.0 mm. Diameter: 3.0 mm to 4.0 mm. Color: Green (RHS 145B/145C) with greyed-purple stripe on one side of pedicel towards inflorescence (RHS 187B).

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDETAM' differs from female parent plant '01-1758' (unpatented) in that 'PHALDETAM' has white whiskers of the lip and a white and yellow apical lobe of the lip, whereas '01-1758' has light purple whiskers of the lip and a yellow and red apical lobe of the lip. Additionally, 'PHALDETAM' has open/free petals, whereas '01-1758' has petals that are almost touching to touching.

'PHALDETAM' differs from male parent plant '06285-01' (unpatented) in that 'PHALDETAM' has a dark purple callus, shorter lip whiskers and a flecked flower, whereas '06285-01' has a yellow-orange dotted callus, longer lip whiskers and an even flower. Additionally, 'PHALDETAM' has a smaller flower than '06285-01'.

'PHALDETAM' differs from commercial variety 'PHALDAMWIL' (U.S. Plant Pat. No. 25,444) in that 'PHALDETAM' has evenly colored whiskers and apical lobe of the lip, and an even petal margin, whereas 'PHALDAMWIL' has dotted whiskers and apical lobe of the lip, and an undulated petal margin.

I claim:

1. A new and distinct variety of *Phalaenopsis* plant named 'PHALDETAM' as illustrated and described herein.

* * * * *